United States Patent [19]
Arai et al.

[11] Patent Number: 5,963,331
[45] Date of Patent: Oct. 5, 1999

[54] SHAPE INPUT DEVICE

[75] Inventors: Kazuhiko Arai, Hachioji; Susumu Tachi, Tsukuba, both of Japan

[73] Assignees: Olympus Optical Co., Tokyo; Susumu Tachi, Tsukuba, both of Japan

[21] Appl. No.: 08/990,964

[22] Filed: Dec. 15, 1997

[30] Foreign Application Priority Data

Dec. 18, 1996 [JP] Japan ................................. 8-338529

[51] Int. Cl.$^6$ ............................. G01B 11/24; G01B 5/34; G01B 11/02; G06F 15/00
[52] U.S. Cl. .......................... 356/376; 356/379; 356/383; 356/384; 364/406; 250/231
[58] Field of Search .................................. 364/406, 806; 340/209; 414/5; 356/376, 379, 383, 384

[56] References Cited

U.S. PATENT DOCUMENTS

| | | | |
|---|---|---|---|
| 4,302,138 | 11/1981 | Zarudiansky | 414/5 |
| 4,988,981 | 1/1991 | Zimmerman et al. | 340/709 |
| 5,184,319 | 2/1993 | Kramer | 364/806 |
| 5,631,861 | 5/1997 | Kramer | 364/406 |

FOREIGN PATENT DOCUMENTS

| | | |
|---|---|---|
| 1-56684 | 12/1989 | Japan . |
| 5-113327 | 5/1993 | Japan . |
| 5-149706 | 6/1993 | Japan . |
| 6-3465 | 1/1994 | Japan . |
| 7-184882 | 7/1995 | Japan . |

*Primary Examiner*—Frank G. Font
*Assistant Examiner*—Roy M. Punnoose
*Attorney, Agent, or Firm*—Frishauf, Holtz, Goodman, Langer & Chick, P.C.

[57] ABSTRACT

A device for inputting a shape of an object includes a base mounted on the object, a flex detecting unit for detecting an amount of flex of the object, and a stretch detecting unit, coupled to the base and to the flex detecting unit, for detecting an amount of stretch between the base and the flex detecting unit which corresponds to an amount of stretch of the object. The stretch detecting unit includes a stretch mechanism which is expanded or contracted in accordance with the stretch of the object, and the amount of stretch of the object is detected based on a detected amount of stretch of the stretch mechanism. The flex detecting unit includes a member which is deformable in an amount corresponding to the amount of flex of the object, and the amount of flex of the object is detected based on a detected amount of deformation of the deformable member.

20 Claims, 5 Drawing Sheets

FIG. 5E

SHAPE INPUT DEVICE

BACKGROUND OF THE INVENTION

The present invention relates to a shape input device which can measure any change in shape of a target object and can input measurement information to, e.g., a measuring instrument.

Conventional shape input devices are disclosed in, e.g., Jpn. Pat. Appln. KOKOKU Publication No. 1-56684 and Jpn. Pat. Appln. KOKAI Publication Nos. 5-113327 and 7-184882. All of these shape input devices have a rod member which can be pivotally set along the joint of, e.g., a wrist or arm, and a detection means which can detect the pivot angle of this rod member. The shape change state of the joint is recognized based on the pivot angle of the rod member which is detected by the detection means when the shape of the joint changes.

A change in joint shape is not a simple shape change component which can be specified by only a change in pivot angle of the rod member. In particular, since motion of the hand or finger is a complicated combination of rotational motion and expanding/contracting motion, it is difficult to obtain the shape change state of the joint of the hand or finger with an angle detection unit having a simple arrangement as described above.

For example, Jpn. Pat. Appln. KOKAI Publication Nos. 5-149706 and 6-3465 disclose a shape input device which can detect the shape change of a hand or finger consisting of a plurality of joints.

The shape input device disclosed in Jpn. Pat. Appln. KOKAI Publication No. 5-149706 has a bend sensor which extends along each finger portion of a flexible glove and the resistance of which changes in accordance with the flexing amount of the corresponding joint of the hand or finger. A change in shape of the hand or finger which is apparently bent the most largely can be detected based on a change in resistance of the bend sensor (this will be called the first prior art).

The shape input device disclosed in Jpn. Pat. Appln. KOKAI Publication No. 6-3465 has conductive gel which is applied on each joint portion of a flexible glove and the resistance of which changes in accordance with the flexing amount of the corresponding joint of the hand or finger. A change in shape of the hand or finger can be detected based on a change in resistance of each conductive gel (this will be called the second prior art).

In the above described first and second prior art references, the bend sensor or conductive gel is directly provided on the flexible glove. Accordingly, when a certain joint flexes, this flexing motion is transmitted to another joint portion through the flexible glove to undesirably change the resistance of the bend sensor or conductive gel at this other joint portion. In particular, in the second prior art reference, the influence of the relative translating displacements of the respective conductive gels, which occur upon flexure of the joints, and the influence of strain produced by the flexing displacements of the joints sometimes mix in the detected resistance. As a result, it is sometimes difficult to precisely input a change in shape of the hand or finger. In this case, a change in shape of the hand or finger may be accurately reproduced by signal processing of input data. With this method, however, the lengths of the respective joints of the hand or finger or the link must be measured in advance in units of users, or the input program must be reset in units of users.

BRIEF SUMMARY OF THE INVENTION

The present invention has been made in order to solve these problems, and has as its object to provide a shape input device which can easily input a change in shape of the target object with high precision.

In order to achieve the above object, according to the present invention, there is provided a shape input device comprising stretch detecting means for detecting an amount of a stretch of the object; flex detecting means for detecting an amount of a flex of the object; and connecting means for jointing the stretch detecting means and the flex detecting means corresponding to the shape of the object.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A shape input device according to the first embodiment of the present invention will be described with reference to FIGS. 1A and 1B, FIGS. 2A to 2C, and FIGS. 3A to 3E.

The shape input device according to this embodiment has at least one shape input assembly 2 which can detect a change in shape of a target object the shape of which changes, and can be detachably attached to the target object. The shape input assembly 2 is formed with at least one expansion/contraction amount detection unit which can detect the extraction/contraction amount of the target object, at least one flexing amount detection unit which can detect the flexing amount of the target object, and a connecting means which can combine the expansion/contraction amount detection unit and the flexing amount detection unit in accordance with the size and shape of the target object.

The shape input device according to this embodiment is formed with a tight-contact means for bringing the shape input assembly 2 into tight contact with the target object. An example of the target object to which the shape input device can be applied includes, e.g., a human hand, finger, and leg, and various types of other variable-shape objects. As an example, this embodiment is applied to a human hand 4 (see FIG. 1B). In this case, as the tight-contact means, a flexible glove 6 (e.g., a silicone rubber glove) is employed which elastically deforms in accordance with the size or shape of the human hand 4 to bring the shape input assembly 2 into tight contact with the human hand 4.

Figure 1A:
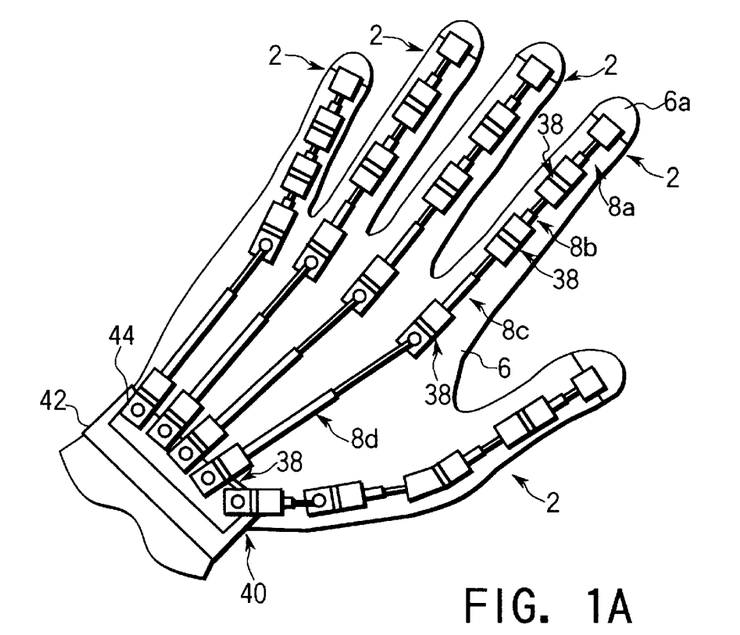
FIG. 1A is a plan view schematically showing the arrangement of a shape input device according to the first embodiment of the present invention.
Figure 1B:
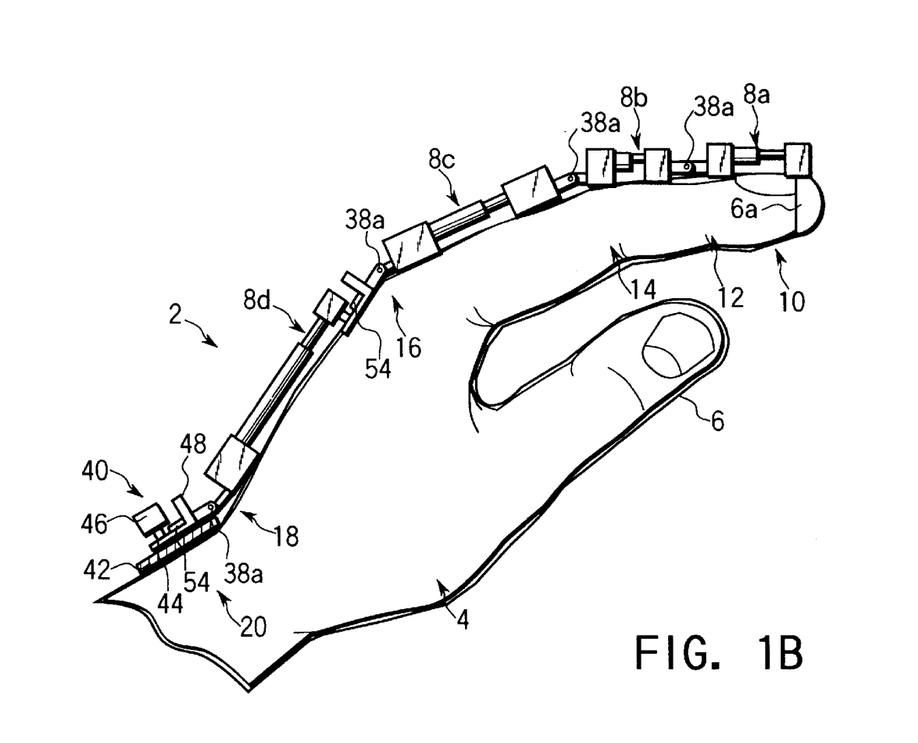
FIG. 1B is a partially sectional side view of FIG. 1A.

As shown in FIG. 1A, in the shape input device of this embodiment, five shape input assemblies 2 extending from the wrist along five fingertips are detachably attached to the flexible glove 6. Since these shape input assemblies 2 have the same arrangement except that their sizes differ from one finger to another, in the following description, the arrangement of only the shape input assembly 2 (see FIG. 1B) extending along the forefinger will be explained as an example.

As shown in FIG. 1B and FIGS. 2A to 2C, the shape input assembly 2 is formed with first to fourth expansion/contraction amount detection units 8a, 8b, 8c, and 8d arranged among the respective joints of the hand 4. More specifically, the first expansion/contraction amount detection unit 8a is arranged between a fingertip 10 and a first joint 12, the second expansion/contraction amount detection unit 8b is arranged between the first joint 12 and a second joint 14, the third expansion/contraction amount detection unit 8c is arranged between the second joint 14 and a third joint 16, and the fourth expansion/contraction amount detection unit 8d is arranged between the third joint 16 and a wrist joint 18. In this embodiment, the joints will be numbered as the first joint 12, the second joint 14, and the third joint 16 from the fingertip 10 toward a wrist 20.

Figure 2A:
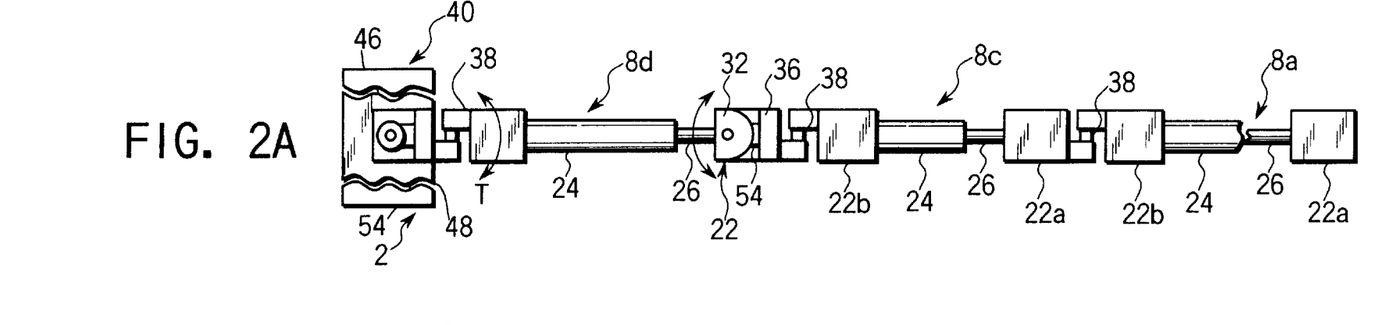
FIG. 2A is a plan showing the practical arrangement of the shape input assembly of the shape input device shown in FIGS. 1A and 1B.
Figure 2B:
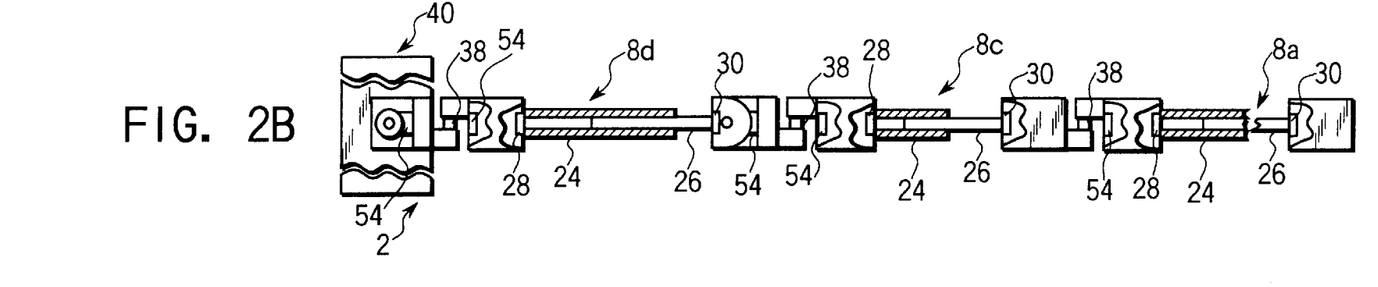
FIG. 2B is a partially cross-sectional view of FIG. 2A.
Figure 2C:
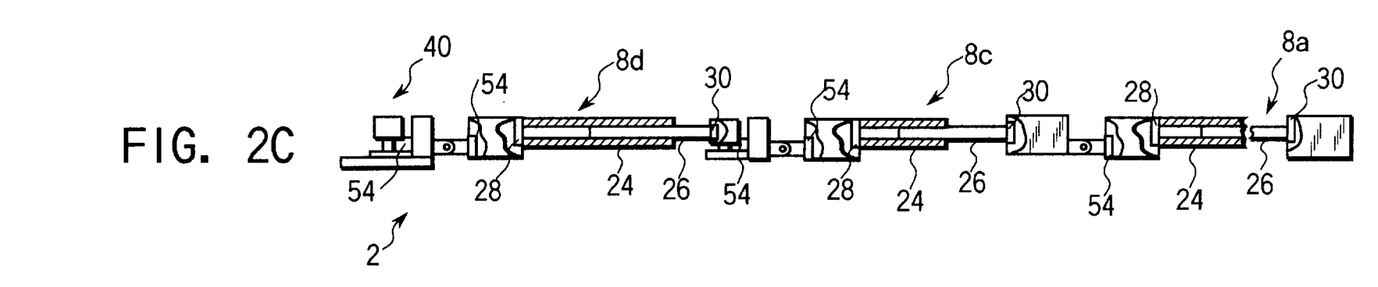
FIG. 2C is a partially longitudinally sectional view of FIG. 2A.

As shown in FIGS. 2A to 2C and FIG. 3C, each of the first to third expansion/contraction amount detection units 8a, 8b, and 8c has a pair of bases 22a and 22b, an expansion/contraction mechanism supported between the bases 22a and 22b, and a detection means capable of optically detecting the expansion/contraction amount of this expansion/contraction mechanism. In this embodiment, of the pair of bases 22a and 22b, one on the fingertip side is called the front base 22a, and one on the wrist side is called the rear base 22b. In FIGS. 2A to 2C, the second expansion/contraction amount detection unit 8b is omitted.

The expansion/contraction mechanism has a hollow guide member 24 extending from the rear base 22b, and a hollow slidable member 26 extending from the front base 22a and slidable in the guide member 24. When the slidable member 26 slides along the guide member 24 relative to it, the distance between the front base 22a and rear base 22b changes relatively. These front and rear bases 22a and 22b are detachably attached to the flexible glove 6 with attaching means (not shown). As the attaching means, for example, an adhesive or Velcro tape can be used.

The detection means has a light-emitting element 28 incorporated in the rear base 22b, and a light-receiving element 30 incorporated in the front base 22a and capable of outputting an electric signal corresponding to the received light amount. The light-emitting element 28 and light-receiving element 30 are arranged to oppose each other such that light emitted by the light-emitting element 28 passes through the guide member 24 and slidable member 26 and enters the light-receiving element 30. The light emission amount of the light-emitting element 28 is preset to a predetermined level so that even when the distance between the front base 22a and rear base 22b becomes the largest, light having a sufficiently large light amount reaches from the light-emitting element 28 to the light-receiving element 30.

According to this detection means, when the expansion/contraction mechanism operates in accordance with a change in shape of the hand 4 and the distance between the front base 22a and rear base 22b changes relatively, the optical characteristics (e.g., the light amount) of light detected by the light-receiving element 30 change. At this time, the relative distance between the front base 22a and rear base 22b is measured by detecting the electric signal output from the light-receiving element 30. The expansion/contraction amounts among the respective joints of the hand 4 can be detected separately based on this relative distance.

The front bases 22a and rear bases 22b of the first to third expansion/contraction amount detection units 8a, 8b, and 8c are respectively detachably attached to the back of the hand of the flexible glove 6 with attaching means (not shown). The front base 22a of the first expansion/contraction amount detection unit 8a is detachably attached to a fingertip holding portion 6a (see FIGS. 1A and 1B) of the flexible glove 6 that holds the fingertip 10. As the attaching means, for example, an adhesive or Velcro tape can be used. When fixing the front bases 22a and rear bases 22b to the flexible glove 6, for example, a fixing adhesive may be used as the attaching means.

Figure 3A:
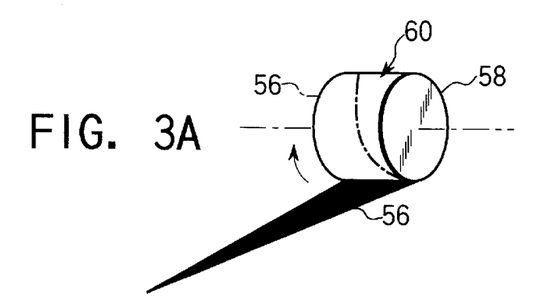
FIGS. 3A and 3B are perspective views showing the arrangement of the detection means of the shape input device shown in FIGS. 1A and 1B.
Figure 3B:
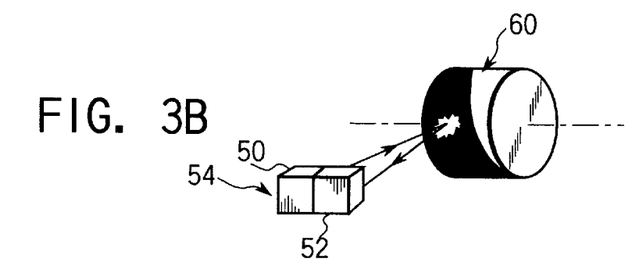
Figure 3C:
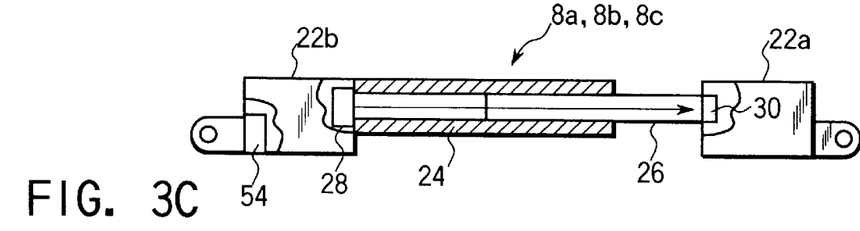
FIG. 3C is a partially sectional view showing the arrangement of the first to third expansion/contraction amount detection units of the shape input device.
Figure 3D:
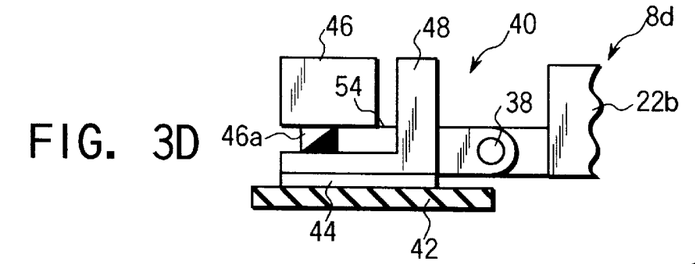
FIG. 3D is a partially sectional view showing the arrangement of the support assembly of the shape input device.
Figure 3E:
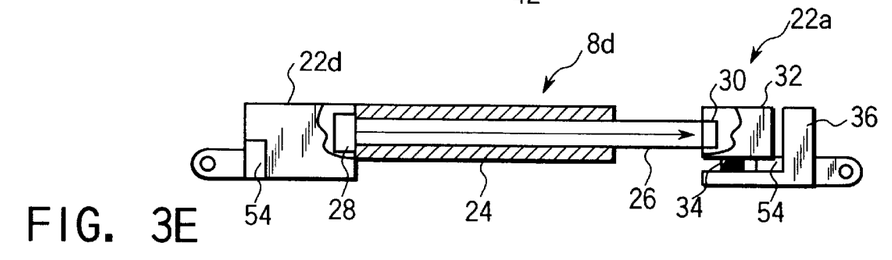
FIG. 3E is a partially sectional view showing the arrangement of the fourth expansion/contraction amount detection unit of the shape input device.

As shown in FIG. 3E, the fourth expansion/contraction amount detection unit 8d is formed such that it can follow the expanding/contracting motion of the back of the hand, and its front base 22a has a pivot base 32, a pivot shaft 34, and a fixed base 36. The pivot base 32 supports the hollow slidable member 26. The pivot shaft 34 is integrally formed on the pivot base 32 to project from it and extends in a direction perpendicularly intersecting the axis of the slidable member 26. The fixed base 36 pivotally supports the pivot shaft 34. The rear base 22b and fixed base 36 of the fourth expansion/contraction amount detection unit 8d are detachably attached to the back of the hand of the flexible glove 6 with the attaching means. Accordingly, the fourth expansion/contraction amount detection unit 8d can pivot in the direction of an arrow S (see FIG. 2A) about the pivot shaft 34 as the center. Since the other arrangements of the fourth expansion/contraction amount detection unit 8d are the same as those of the first to third expansion/contraction amount detection units 8a, 8b, and 8c, they are denoted by the same reference numerals as those of the first to third expansion/contraction amount detection units 8a, 8b, and 8c, and a detailed description thereof will be omitted.

These first to fourth expansion/contraction amount detection units 8a, 8b, 8c, and 8d are pivotally connected to each other with four connecting means 38. The respective connecting means 38 are positioned to correspond to the first joint 12, the second joint 14, the third joint 16, and the wrist joint 18 (see FIG. 1B).

As shown in FIG. 1B and FIGS. 2A to 2C, each connecting means 38 is formed with a connecting shaft 38a extending in a direction perpendicularly intersecting the axis of the guide member 24 and slidable member 26.

More specifically, in the first and second expansion/contraction amount detection units 8a and 8b, the rear base 22b of the first expansion/contraction amount detection unit 8a and the front base 22a of the second expansion/contraction amount detection unit 8b are connected to each other through the corresponding connecting shaft 38a, so that they can pivot relative to each other about the connecting shaft 38a as the center in accordance with the flexing state of the first joint 12. Similarly, in the second and third expansion/contraction amount detection units 8b and 8c, the rear base 22b of the second expansion/contraction amount detection unit 8b and the front base 22a of the third expansion/contraction amount detection unit 8c are connected to each other through the corresponding connecting shaft 38a, so that they can pivot relative to each other about the connecting shaft 38a as the center in accordance with the flexing state of the second joint 14. In the third and fourth expansion/contraction amount detection units 8c and 8d, the rear base 22b of the third expansion/contraction amount detection unit 8c and the fixed base 36 of the fourth expansion/contraction amount detection unit 8d are connected to each other through the corresponding connecting shaft 38a, so that they can pivot relative to each other about the connecting shaft 38a as the center in accordance with the flexing state of the third joint 16. The fourth expansion/contraction amount detection unit 8d is pivotally supported by a support assembly 40 (to be described later) through the corresponding connecting shaft 38a arranged on the wrist joint 18.

As shown in FIG. 3D, the support assembly 40 has a support reference holder 42, a fixed base 44, and a pivot base 48. The support reference holder 42 is detachably attached to the wrist 20 (see FIG. 1B) of the flexible glove 6 with an attaching means (not shown). The fixed base 44 is formed on the support reference holder 42 on the side of the back of the hand. The pivot base 48 is pivotally supported on the fixed base 44 with a fixing pin 46 perpendicularly intersecting the corresponding connecting shaft 38a. The pivot base 48 is connected to the rear base 22b of the fourth expansion/contraction amount detection unit 8d through the corresponding connecting shaft 38a. Accordingly, the fourth expansion/contraction amount detection unit 8d can pivot in the direction of an arrow T (see FIG. 2A) about the fixing pin 46 as the center so as to follow the stretching expanding/contracting motion of the back of the hand. As the attaching means, for example, an adhesive or Velcro tape can be used.

With the arrangement described above, in accordance with the flexing change of the first joint 12, the second joint 14, the third joint 16, and the wrist joint 18, the first to fourth expansion/contraction amount detection units 8a, 8b, 8c, and 8c pivot relative to each other about the connecting shafts 38a of the respective connecting means 38 described above as the center.

The flexing amount detection unit incorporated in this embodiment has a detection means that can optically detect the flexing change of the respective joints 12, 14, 16, and 18 of the hand based on the pivot amounts of the connecting shafts 38a.

As shown in FIGS. 2A to 2C and FIGS. 3A to 3E, the detection means of the flexing amount detection unit has a light-receiving/emitting unit 54 (see FIG. 3B) and a light amount changing means. The light-receiving/emitting unit 54 is incorporated in the rear base 22b of each of the first to fourth expansion/contraction amount detection units 8a, 8b, 8c, and 8d and is formed by integrating a light-emitting element 50 and a light-receiving element 52. The light amount changing means changes the optical characteristics (e.g., the light amount) of the reflected light in accordance with the pivot amount of the corresponding connecting shaft 38a. This light amount changing means is pattern-printed on the circumference surface of the corresponding connecting shaft 38a in advance.

As shown in, e.g., FIGS. 3A and 3B, the light amount changing means is formed by printing a density pattern 60, which is identical to a density region formed when a black right-angled triangular paper piece 56 is wound on a white cylindrical member 58, on the outer circumferential surface of each connecting shaft 38a.

In this flexing amount detection unit, light emitted by the light-emitting element 50 is reflected by the density pattern 60 and is received by the light-receiving element 52. In this state, when the respective connecting shafts 38a pivot in accordance with the flexing changes of the respective joints of the hand, the density patterns 60 printed on the respective connecting shafts 38a move in the same manner, and the optical characteristics (e.g., the light amount) of the light reflected by the density patterns 60 change. The pivot amounts of the respective connecting shafts 38a are detected based on the changes in light amount of the reflected light received by the light-receiving elements 52. The flexing amounts of the first joint 12, the second joint 14, the third joint 16, and the wrist joint 18 are detected separately based on the pivot amounts of the respective connecting shafts 38a.

As shown in FIGS. 3D and 3E, this embodiment has a pivot amount detection unit for optically detecting the pivot amount of the fourth expansion/contraction amount detection unit 8d obtained upon the expanding/contracting motion of the back of the hand. This pivot amount detection unit can separately detect the pivot amount of the pivot base 32 formed on the front base 22a of the fourth expansion/contraction amount detection unit 8d and the pivot amount of the pivot base 48 of the support assembly 40.

More specifically, the pivot shaft 34 formed on the pivot base 32 of the fourth expansion/contraction amount detection unit 8d to project from it has a light amount changing means (see FIG. 3A) similar to that described above, and the fixed base 36 for pivotally supporting this pivot shaft 34 has a light-receiving/emitting unit 54 similar to that described above. The pivot amount of the pivot shaft 34 is detected based on a change in light amount of the light amount changing means detected by this light-receiving/emitting unit 54. The fixing pin 46 for pivotally supporting the pivot base 48 of the support assembly 40 has a light amount changing means (see FIG. 3A) like that described above on its fixed shaft 46a, and a light-receiving/emitting unit 54 similar to that described above is arranged on the pivot base 48. The pivot amount of the pivot base 48 with respect to the fixing pin 46 is detected based on a change in light amount of the light amount changing means detected by this light-receiving/emitting unit 54.

In this manner, according to the shape input device of this embodiment, complicated stretching expanding/contracting motion, pivot motion, and flexing motion that occur upon a change in shape of the hand 4 can be detected separately, so that changes in shape of the hand 4 can be input highly precisely and accurately.

The present invention is not limited to the arrangement of the above embodiment, and various changes and modifications may be made within the scope which includes no new matter. For example, the above embodiment exemplifies a case wherein a change in shape of the left hand is to be input. However, if the device of the present invention is attached to the right hand, each of the right and left hands, or one finger according to each application purpose, a change in shape of the right hand, the right and left hands, or one finger can be input. In the above embodiment, the device according to the present invention is attached to the hand 4 through the flexible glove 6. However, this device can be directly attached to the hand 4 without using a flexible glove 6 but with, e.g., a Velcro tape.

As a modification of the detection means that detect the expansion/contraction amounts of the first to fourth expansion/contraction amount detection units 8a, 8b, 8c, and 8d, for example, if light-receiving/emitting units 54 similar to that shown in FIG. 3B are used in place of the light-emitting element 28, reflection type detection means can be employed. In this case, it is preferable to remove the light-receiving elements 30 and employ columnar slidable members 26 and to form reflection films on the distal end faces (surfaces facing the light-receiving/emitting units 54) of the slidable members 26. According to this modification, when irradiating light to the reflection films, the relative distance between the front base 22a and rear base 22b is measured by detecting the change in light amount of light reflected by these reflection films.

Changes in relative distance between the front bases 22a and rear bases 22b of the respective pairs may be measured by, e.g., linear encoders, and the expansion/contraction amounts of the first to fourth expansion/contraction amount detection units 8a, 8b, 8c, and 8d may be detected based on the obtained pulse counts of the linear encoders obtained by measurement. When the pulse counts are counted in this manner, changes in relative distance can be measured without being influenced by noise.

The resistive force may be indicated to the device user by feeding a fluid, e.g., positive or negative pressure air or oil, from a compressor into the guide members 24 and slidable members 26 of the first to fourth expansion/contraction amount detection units 8a, 8b, 8c, and 8d. In this case, force sensors that measure the force acting in the guide members 24 and slidable members 26 from the pressure of the fluid may be provided, and the output information from the power sensors may be subjected to predetermined arithmetic processing, so that force information can be indicated to the device user.

Furthermore, each expansion/contraction mechanism constituted by the guide member 24 and slidable member 26 may be formed with, e.g., an air valve, and the resistive force may be indicated to the device user by opening/closing this air valve.

Figure 4:
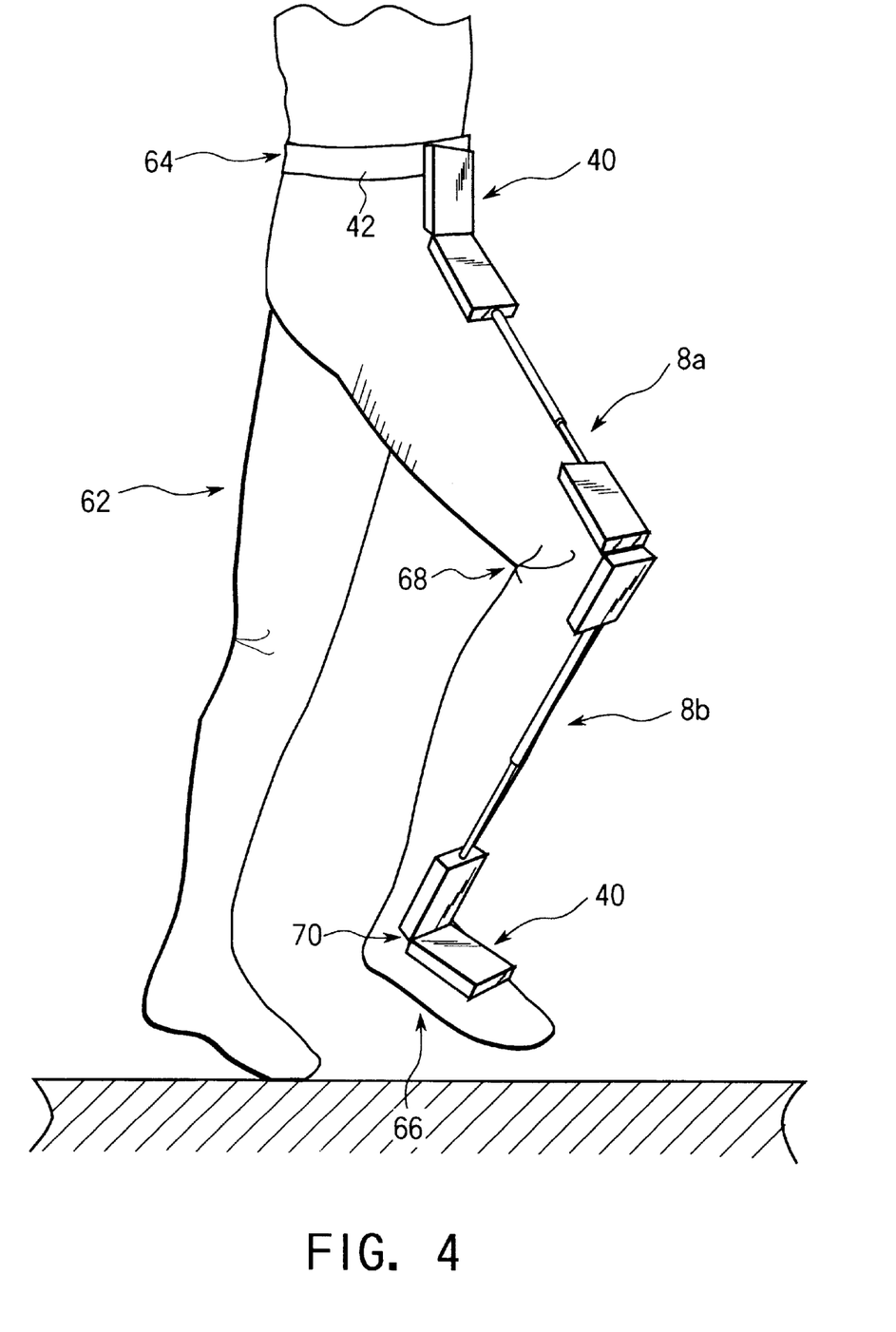
FIG. 4 is a perspective view showing a state wherein the shape input device shown in FIGS. 1A and 1B is attached to a human leg.

As shown in FIG. 4, the shape input device according to the present invention may be attached to a human leg 62, so that a change in shape of the leg 62 can be input. In this case, a support assembly 40 is attached to a support reference holder 42 attached to a human waist 64, and another support assembly 40 is attached to the instep of a human foot 66. For example, a first expansion/contraction amount detection unit 8a is arranged to extend from the human waist 64 to a knee joint 68 and, for example, a second expansion/contraction amount detection unit 8b is arranged to extend from the knee joint 68 to an ankle joint 70. The support assemblies 40 and the first and second expansion/contraction amount detection units 8a and 8b are connected to each other with connecting means. With this arrangement, complicated stretching expanding/contracting motion and flexing motion that accompany a change in shape of the leg 62 can be detected separately, so that changes in shape of the leg 62 can be input highly precisely and accurately.

A shape input device according to the second embodiment of the present invention will be described with reference to FIGS. 5A to 5E. In the description of the second embodiment, portions that are identical to those shown in the first embodiment are denoted by the same reference numerals as in the first embodiment, and a detailed description thereof will be omitted.

Figure 5A:
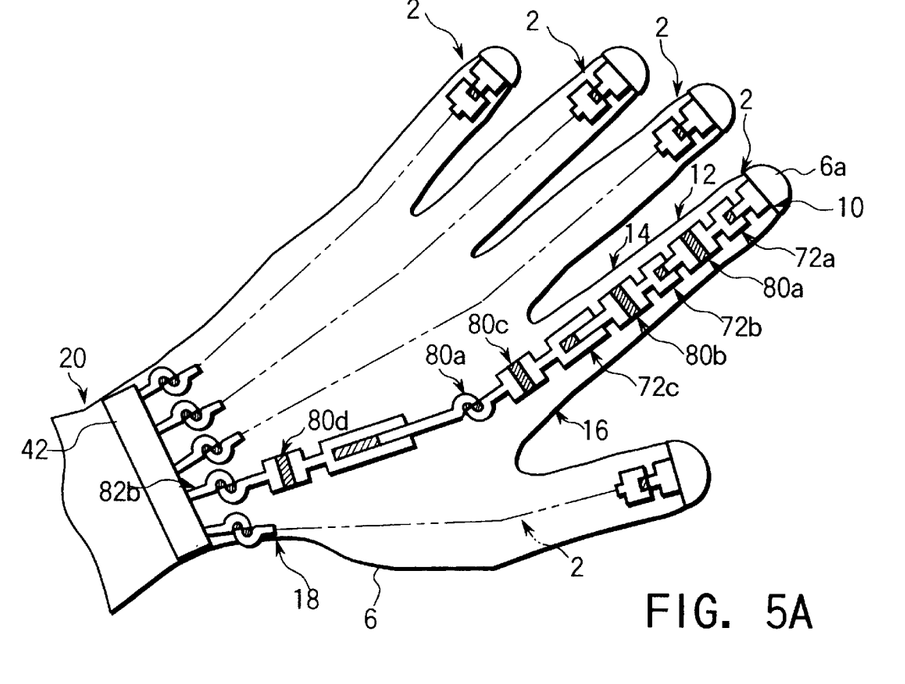
FIG. 5A is a plan view schematically showing the arrangement of a shape input device according to the second embodiment of the present invention.

As shown in FIG. 5A, the shape input device of this embodiment is adapted to a human hand (see reference numeral 4 of FIG. 1B) as the target object, in the same manner as in the first embodiment, and five shape input assemblies 2 extending from a wrist 20 along five fingertips 10 are brought into tight contact with the hand with a flexible glove 6 (e.g., a silicone rubber glove). Since these shape input assemblies 2 have the same arrangement except that their sizes differ from one finger to another, in the following description, the arrangement of only the shape input assembly 2 extending along the forefinger will be explained as an example.

The shape input assembly 2 is formed with first to fourth expansion/contraction amount detection units 72a, 72b, 72c, and 72d arranged among the respective joints of the hand. More specifically, the first expansion/contraction amount detection unit 72a is arranged between the fingertip 10 and a first joint 12, the second expansion/contraction amount detection unit 72b is arranged between the first joint 12 and a second joint 14, the third expansion/contraction amount detection unit 72c is arranged between the second joint 14 and a third joint 16, and the fourth expansion/contraction amount detection unit 72d is arranged between the third joint 16 and a wrist joint 18. In this embodiment, although an actual hand is not disclosed in FIG. 5A, assuming that a hand is placed in the flexible glove 6 to be in tight contact with it, the joints will be numbered as the first joint 12, the second joint 14, and the third joint 16 from the fingertip 10 toward the wrist 20.

Figure 5B:
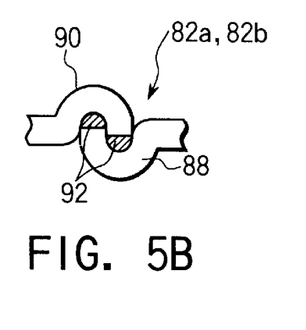
FIG. 5B is a view showing the arrangement of the first and second pivot amount detection units of the shape input device.
Figure 5C:
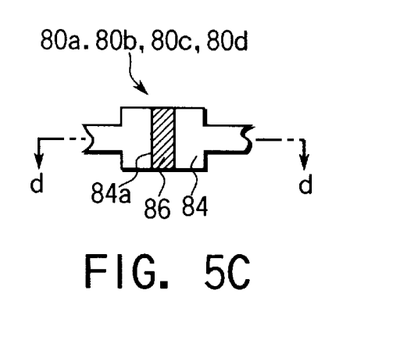
FIG. 5C is a view showing the arrangement of a connecting means incorporated with a flexing amount detection unit.
Figure 5D:
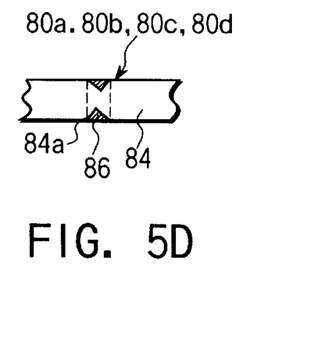
FIG. 5D is a sectional view taken along the line d—d of FIG. 5C.
Figure 5E:
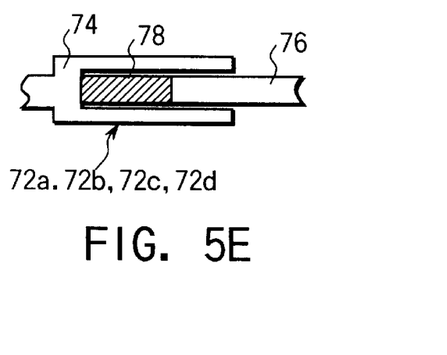
FIG. 5E is a view showing the arrangement of the first to fourth expansion/contraction amount detection units of the shape input device.

As shown in FIG. 5E, each of the first to fourth expansion/contraction amount detection units 72a, 72b, 72c, and 72d has an expansion/contraction mechanism which expands/contracts in accordance with a change in shape of the hand, and a detection means which can electrically detect the expansion/contraction amount of this expansion/contraction amount.

The expansion/contraction mechanism has a bottomed cylindrical guide member 74 (to be referred to as a guide member hereinafter) and a columnar slidable member 76 (to be referred to as a slidable member hereinafter) which can slide in the guide member 74. The guide member 74 and slidable member 76 are attached to the flexible glove 6 such that they linearly move relative to each other without rotation. The slidable member 76 of the first expansion/contraction amount detection unit 72a is detachably attached to a fingertip holding portion 6a (see FIG. 5A) of the flexible glove 6 that holds the fingertip 10.

The detection means has a conductive elastic member 78 (e.g., a conductive rubber member). The conductive elastic member 78 is accommodated in the guide member 74 so as to connect the guide member 74 and slidable member 76 to each other. When the conductive elastic member 78 is elastically deformed in accordance with the relative sliding state of the slidable member 76, its resistance changes.

With this arrangement, when the guide member 74 and slidable member 76 linearly move, upon a change in shape of the hand, in directions to separate relative to each other, a tensile force or compression force acts on the conductive elastic member 78. At this time, the relative distance between the guide member 74 and slidable member 76 is measured by detecting the resistance of the conductive elastic member 78 which changes in accordance with the tensile force or compression force. The expansion/contraction amounts among the respective joints of the hand can be detected separately based on this relative distance.

The first to third expansion/contraction amount detection units 72a, 72b, and 72c are integrally connected to each other through first to third connecting means 80a, 80b, and 80c, and the fourth expansion/contraction amount detection unit 72d is supported through first and second pivot amount detection units 82a and 82b that pivot upon stretching expanding/contracting motion of the back of the hand. More specifically, the slidable member 76 of the fourth expansion/contraction amount detection unit 72d is pivotally connected to the third connecting means 80c through the pivot amount detection unit 82a, and the guide member 74 of the fourth expansion/contraction amount detection unit 72d is pivotally connected to the second pivot amount detection unit 82b through a fourth connecting means 80d. The second pivot amount detection unit 82b is integrally supported by a support reference holder 42, detachably attached to the wrist 20 of the flexible glove 6, with an attaching means (not shown).

The first to fourth connecting means 80a, 80b, 80c, and 80d are positioned to correspond to the first joint 12, the second joint 14, the third joint 16, and the wrist joint 18, respectively, and can elastically deform in accordance with the flexing amounts of the respective joints of the hand.

Flexing amount detection units are incorporated in this embodiment to electrically detect the flexing amounts of the respective joints of the hand based on the elastic deformation amounts of the respective connecting means.

As shown in FIGS. 5C and 5D, each of the connecting means 80a, 80b, 80c, and 80d in which the flexing amount detection unit is incorporated has an elastic member 84, e.g., a resin member. Notched portions 84a each having a triangular section are formed at substantially the central portion of the elastic member 84. The two sides of the elastic member 84 are elastically deformed relative to each other about the notched portions 84a as the center. FIG. 5D is a sectional view taken along the line d—d of FIG. 5C.

Each flexing amount detection unit has detection means incorporated in the notched portions 84a. The detection means have conductive elastic members 86 (e.g., conductive rubber members). When the conductive elastic members 86 elastically deform in accordance with the shape change state of the elastic member 84, their resistance change.

With this arrangement, when the elastic member 84 relatively and elastically deforms about the notched portions 84a as the center upon a change in shape of the hand, a tensile force or compression force acts on the conductive elastic members 86. At this time, the deformation amount of the elastic member 84 is measured by detecting the resistance of each conductive elastic member 86 that changes in accordance with the tensile force or compression force. The flexing amount of each joint of the hand can be detected separately based on this deformation amount.

As shown in FIG. 5B, each of the first and second pivot amount detection units 82a and 82b has first and second first hook members 88 and 90 interlocked with each other, and a detection means for pivotally connecting the first and second first hook members 88 and 90 to each other. This detection means has a conductive elastic member 92 (e.g., a conductive rubber member). When the conductive elastic member 92 elastically deforms in accordance with the pivot state of the first and second first hook members 88 and 90, its resistance changes. More specifically, the first hook member 88 of the first pivot amount detection unit 82a is integrally connected to the third connecting means 80c, and the second hook member 90 of the first pivot amount detection unit 82a to the slidable member 76 of the fourth expansion/contraction amount detection unit 72d. The first hook member 88 of the second pivot amount detection unit 82b is integrally connected to the fourth connecting means 80d, and the second hook member 90 of the second pivot amount detection unit 82b to the support reference holder 42.

With this arrangement, when the first and second hook members 88 and 90 pivot relative to each other upon a change in shape (stretching expanding/contracting motion) of the hand, a tensile force or compression force acts on the conductive elastic member 92. At this time, the pivot amounts of the first and second first hook members 88 and 90 are measured by detecting the resistance of the conductive elastic member 92 that changes in accordance with the tensile force or compression force. The pivot amounts of the respective joints of the hand obtained upon a change in shape of the hand can be detected separately based on this pivot amounts.

In this manner, according to the shape input device of this embodiment, complicated stretching expanding/contracting motion, pivot motion, and flexing motion that occur upon a change in shape of the hand can be detected separately, so that changes in shape of the hand can be input highly precisely and accurately.

The present invention is not limited to the arrangement of the above embodiment, and various changes and modifications may be made within the scope which includes no new matter. For example, the above embodiment exemplifies a case wherein a change in shape of the left hand is to be input. However, if the device of the present invention is attached to the right hand, each of the right and left hands, or one finger according to the application purpose, a change in shape of the right hand, the right and left hands, or one finger can be input. In the above embodiment, the device according to the present invention is attached to the hand through the flexible glove 6. However, this device can be directly attached to the hand without using a flexible glove 6 but with, e.g., a Velcro tape.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A device for inputting a shape of an object, comprising:
   a base mounted on the object;
   flex detecting means for detecting an amount of flex of the object; and
   stretch detecting means, coupled to the base and to the flex detecting means, for detecting an amount of stretch between the base and the flex detecting means which corresponds to an amount of stretch of the object.

2. The device of claim 1, wherein the stretch detecting means includes a stretch mechanism which is expanded or contracted in accordance with the stretch of the object, and wherein the amount of stretch of the object is detected based on a detected amount of stretch of the stretch mechanism.

3. The device of claim 2, wherein the stretch mechanism includes a guide member and a member slidable along the guide member.

4. The device of claim 3, wherein the guide member includes a light source at an end thereof and the slidable member includes a photo-detector at an end thereof for receiving light from the light source, and wherein the amount of stretch of the object is detected based on a position of the slidable member determined in accordance with a signal from the photodetector.

5. The device of claim 2, wherein the stretch mechanism includes a member which is deformable in accordance with the amount of stretch of the object, and wherein the amount of stretch of the object is detected based on a detected amount of deformation of the deformable member.

6. The device of claim 5, wherein the deformable member comprises a conductive elastic member, and wherein the amount of stretch of the object is detected based on a change of resistance of the conductive elastic member.

7. The device of claim 1, wherein the flex detecting means includes a member which is deformable in an amount corresponding to the amount of flex of the object, and wherein the amount of flex of the object is detected based on a detected amount of deformation of the deformable member.

8. The device of claim 7, wherein the deformable member comprises a conductive elastic member, and wherein the amount of flex of the object is detected based on a change of resistance of the conductive elastic member.

9. The device of claim 7, wherein the deformable member includes a first shaft having a rotation axis with a pattern on a surface thereof and a second shaft pivotally connected to the rotation axis, and wherein the amount of flex of the object is detected using the pattern.

10. The device of claim 1, further comprising rotation detecting means for detecting a rotation of the object in a direction different from a direction of the flex of the object, said rotation detecting means being serially connected to the flex detecting means and the stretch detecting means.

11. The device of claim 10, wherein the rotation detecting means includes a member which is deformable in an amount corresponding to an amount of the rotation of the object, and wherein the amount of rotation of the object is detected based on a detected amount of deformation of the deformable member.

12. The device of claim 11, wherein the deformable member comprises a conductive elastic member, and wherein the amount of rotation of the object is detected based on a change of resistance of the conductive elastic member.

13. A device for inputting a shape of an object, comprising:

two flex detecting means for detecting an amount of flex of the object; and stretch detecting means, connected between the two flex detecting means, for detecting an amount of stretch between the two flex detecting means which corresponds to an amount of stretch of the object.

14. The device of claim 13, wherein the stretch detecting means includes a stretch mechanism which is expanded or contracted in accordance with the stretch of the object, and wherein the amount of stretch of the object is detected based on a detected amount of stretch of the stretch mechanism.

15. The device of claim 14, wherein the stretch mechanism includes a guide member and a member slidable along the guide member.

16. The device of claim 14, wherein the stretch mechanism includes a member which is deformable in accordance with the amount of stretch of the object, and wherein the amount of stretch of the object is detected based on a detected amount of deformation of the deformable member.

17. The device of claim 13, wherein the flex detecting means includes a member which is deformable in an amount corresponding to the amount of flex of the object, and wherein the amount of flex of the object is detected based on a detected amount of deformation of the deformable member.

18. The device of claim 17, wherein the deformable member comprises a conductive elastic member, and wherein the amount of flex of the object is detected based on a change of resistance of the conductive elastic member.

19. The device of claim 13, further comprising rotation detecting means for detecting a rotation of the object in a direction different from a direction of the flex of the object, said rotation detecting means being serially connected to the flex detecting means and the stretch detecting means.

20. The device of claim 19, wherein the rotation detecting means includes a member which is deformable in an amount corresponding to an amount of the rotation of the object, and wherein the amount of rotation of the object is detected based on a detected amount of deformation of the deformable member.

* * * * *

UNITED STATES PATENT AND TRADEMARK OFFICE
CERTIFICATE OF CORRECTION

PATENT NO. : 5,963,331
DATED : October 5, 1999
INVENTOR(S) : ARAI et al.

It is certified that error appears in the above-identified patent and that said Letters Patent is hereby corrected as shown below:

On the title page,

Item [73] Assignees, after "Olympus Optical Co.,"
insert --Ltd.--.

Signed and Sealed this

Twentieth Day of February, 2001

Attest:

NICHOLAS P. GODICI

Attesting Officer

Acting Director of the United States Patent and Trademark Office